United States Patent
Scott

(10) Patent No.: US 7,236,616 B1
(45) Date of Patent: Jun. 26, 2007

(54) BIOMETRIC PIEZO SCANNER

(75) Inventor: Walter G Scott, North Palm Beach, FL (US)

(73) Assignee: Cross Match Technologies, Inc., Palm Beach Gardens, FL (US)

( * ) Notice: Subject to any disclaimer, the term of this patent is extended or adjusted under 35 U.S.C. 154(b) by 423 days.

(21) Appl. No.: 10/049,100

(22) PCT Filed: Aug. 9, 2000

(86) PCT No.: PCT/US00/21658

§ 371 (c)(1),
(2), (4) Date: Feb. 8, 2002

(87) PCT Pub. No.: WO01/10296

PCT Pub. Date: Feb. 15, 2001

Related U.S. Application Data

(60) Provisional application No. 60/147,497, filed on Aug. 9, 1999.

(51) Int. Cl.
*G06K 9/00* (2006.01)
*G01P 15/125* (2006.01)

(52) U.S. Cl. .................... 382/124; 73/514.32; 361/280

(58) Field of Classification Search ........ 382/124–134; 73/514.32; 361/280–330; 600/468, 465, 600/453, 463
See application file for complete search history.

(56) References Cited

U.S. PATENT DOCUMENTS

| | | | |
|---|---|---|---|
| 4,316,115 A | 2/1982 | Wilson et al. | 310/327 |
| 4,394,773 A | 7/1983 | Ruell | 382/4 |

(Continued)

FOREIGN PATENT DOCUMENTS

DE   197 50 179 A1   2/1999

(Continued)

OTHER PUBLICATIONS

Davidsen, R. and Smith, S., "Two-Dimensional Array for Medical Ultrasound Using Multilayer Flexible Circuit Interconnection," *IEEE Transactions on Ultrasonics Ferroelectrics, and Frequency Control*, IEEE, vol. 45, No. 2, pp. 338-348 (Mar. 1998).

(Continued)

*Primary Examiner*—Bhavesh M Mehta
*Assistant Examiner*—Aaron Carter
(74) *Attorney, Agent, or Firm*—Sterne, Kessler, Goldstein & Fox P.L.L.C.

(57) ABSTRACT

A piezoelectric thin film sensor array is used to scan and capture biometric data, for example, a fingerprint image. In one embodiment, a multi-layer structure includes a PVDF layer in between two conductor grids arranged orthogonally to one another. Urethane can be added to one side where a finger is placed. A foam substrate can be used as a support. In one feature, the PVDF, and grids can be peeled off like a label for easy replacement. Multiplexers are switched to scan the sensor. A single pixel or a group of pixels can be detected and output to an image memory. The presence of a fingerprint ridge is detected by virtue of a ring-down oscillation that arises from reflection when an electric field is applied to the piezoelectric thin film sensor array at a pixel in contact with the fingerprint ridge. For example, such a ring-down value associated with a fingerprint ridge can be detected at about 150 ns. (or 5 cycles at 30 MHZ). Other reflections indicative of additional biometrics (e.g. from tissue, blood, bone, fingernail, etc.) can also be detected. A Doppler effect due to reflections from circulating blood can also be detected. Such a Doppler effect can provide further information about direction and speed of blood circulation. An instantaneous pyroelectric effect can also be detected to indicate a live finger presence.

14 Claims, 6 Drawing Sheets

U.S. PATENT DOCUMENTS

| | | | |
|---|---|---|---|
| 4,429,413 A * | 1/1984 | Edwards | 382/124 |
| 4,499,394 A | 2/1985 | Koal | |
| 4,539,554 A | 9/1985 | Jarvis et al. | |
| 4,555,953 A | 12/1985 | Dario et al. | |
| 4,634,917 A | 1/1987 | Dvorsky et al. | |
| 4,643,028 A | 2/1987 | Kondo et al. | |
| 4,709,342 A | 11/1987 | Hosoda et al. | |
| 4,814,661 A | 3/1989 | Ratzlaff et al. | |
| 4,849,668 A | 7/1989 | Crawley et al. | |
| 5,055,838 A | 10/1991 | Wise et al. | |
| 5,079,949 A * | 1/1992 | Tamori | 73/172 |
| 5,224,174 A | 6/1993 | Schneider et al. | 382/5 |
| 5,240,004 A * | 8/1993 | Walinsky et al. | 600/467 |
| 5,273,045 A | 12/1993 | Chihara et al. | 128/662.06 |
| 5,305,752 A * | 4/1994 | Spivey et al. | 600/448 |
| 5,311,095 A | 5/1994 | Smith et al. | 310/334 |
| 5,339,051 A | 8/1994 | Koehler et al. | |
| 5,365,154 A | 11/1994 | Schneider et al. | 318/103 |
| 5,389,849 A * | 2/1995 | Asano et al. | 310/323.21 |
| 5,421,335 A | 6/1995 | Wild | 128/662.03 |
| 5,424,596 A | 6/1995 | Mendenhall et al. | |
| 5,456,256 A | 10/1995 | Schneider et al. | 128/660.09 |
| 5,500,635 A | 3/1996 | Mott | |
| 5,515,738 A | 5/1996 | Tamori | 73/862.046 |
| 5,526,701 A * | 6/1996 | Tamori | 73/862.046 |
| 5,552,274 A | 9/1996 | Oyama et al. | |
| 5,578,761 A | 11/1996 | Clark, Jr. et al. | |
| 5,587,533 A | 12/1996 | Schneider et al. | 73/614 |
| 5,623,930 A | 4/1997 | Wright et al. | 128/661.1 |
| 5,647,364 A | 7/1997 | Schneider et al. | 128/660.09 |
| 5,673,041 A * | 9/1997 | Chatigny et al. | 341/22 |
| 5,689,576 A | 11/1997 | Schneider et al. | 382/124 |
| 5,760,530 A | 6/1998 | Kolesar | |
| 5,844,287 A * | 12/1998 | Hassan et al. | 257/419 |
| 5,902,240 A * | 5/1999 | Ishii et al. | 600/438 |
| 5,935,071 A | 8/1999 | Schneider et al. | 600/445 |
| 5,971,927 A | 10/1999 | Mine | 600/455 |
| 6,061,464 A * | 5/2000 | Leger | 382/124 |
| 6,095,979 A * | 8/2000 | Ohtomo | 600/449 |
| 6,111,342 A | 8/2000 | Muramatsu et al. | |
| 6,117,075 A * | 9/2000 | Barnea | 600/300 |
| 6,131,464 A * | 10/2000 | Pare et al. | 73/714 |
| 6,289,114 B1 * | 9/2001 | Mainguet | 382/124 |
| 6,296,610 B1 | 10/2001 | Schneider et al. | 600/445 |
| 6,411,726 B1 * | 6/2002 | Pires | 382/124 |
| 6,437,583 B1 * | 8/2002 | Tartagni et al. | 324/687 |
| 6,459,804 B2 * | 10/2002 | Mainguet | 382/124 |
| 6,461,314 B1 | 10/2002 | Pant et al. | |
| 6,517,487 B1 * | 2/2003 | Mazess et al. | 600/449 |
| 6,522,773 B1 * | 2/2003 | Houdeau | 382/124 |
| 6,714,666 B1 * | 3/2004 | Morimura et al. | 382/124 |
| 6,817,130 B2 * | 11/2004 | Ivanov | 42/70.06 |
| 2001/0026636 A1 * | 10/2001 | Mainguet | 382/124 |

FOREIGN PATENT DOCUMENTS

| | | |
|---|---|---|
| EP | 0 649 116 A1 | 4/1995 |
| JP | 7-059769 | 3/1995 |
| JP | 8-336534 | 12/1995 |
| WO | WO 01/18740 A1 | 3/2001 |
| WO | WO 01/19016 A1 | 3/2001 |
| WO | WO01/67383 A1 | 9/2001 |
| WO | WO 01/91626 A2 | 12/2001 |
| WO | WO02/12660 A1 | 2/2002 |
| WO | WO02/48485 A1 | 5/2002 |
| WO | WO03/15011 A1 | 2/2003 |

OTHER PUBLICATIONS

Schneider et al., "Live Scan Fingerprint Imagery Using High Resolution C-Scan Ultrasonography," *Proceedings of the 25th Annual 1991 IEEE Int'l Carnahan Conference on Security Technology*, IEEE, Oct. 1-3, 1991, Taipei, Taiwan, pp. 89-95.

Patent Abstract of Japanese Publication No. 08336534, Japanese Patent Office, 1 page (Dec. 1996).

Patent Abstract of Japanese Publication No. 07059769, Japanese Patent Office, 1 page (Mar. 1995).

Gary Roethenbaugh, "Biometrics Explained," v. 2.0, International Computer Security Association, Carlisle, PA (1998), pp. 1-34.

Dialog File 349 (PCT Full Text) (1 page) English Language abstract of Patent WO 9910874, published Mar. 4, 1999.

Gary Roethenbaugh, "Biometrics Explained," v. 2.0, International Computer Security Association, Carlisle, PA (1998), pp. 1-24 and 27-34.

* cited by examiner

BIOMETRIC PIEZO SCANNER

This application claims the benefit of the filing date of U.S. Provisional Application Ser. No. 60/147,497, filed 9 Aug. 1999, which is hereby incorporated by reference in its entirety.

BACKGROUND OF THE INVENTION

1. Field of the Invention

The present invention relates generally to fingerprint scanning and imaging. More specifically, this invention relates to a piezoelectric film used within a fingerprint scanner.

2. Related Art

Biometrics are a group of technologies that provide a high level of security. Fingerprint capture and recognition is an important biometric technology. Law enforcement, banking, voting, and other industries increasingly rely upon fingerprints as a biometric to recognize or verify identity. See, *Biometrics Explained*, v. 2.0, G. Roethenbaugh, International Computer Society Assn. Carlisle, Pa. 1998, pages 1–34 (incorporated herein by reference in its entirety). A number of companies are currently active in biometric finger technologies. See, a listing of companies published by Biometric Technology Today (Btt™), two pages, 1999 (http://www.sjbresearch.com).

Optical fingerprint scanners are available that detect a reflected optical image of a fingerprint. To capture a quality image at a sufficiently high resolution, optical fingerprint scanners require at minimum optical components (e.g., lenses), an illumination source, and an imaging camera. Such components add to the overall cost of a fingerprint scanner. Mechanical structures to maintain alignment also increase manufacturing and maintenance costs.

Solid-state silicon-based transducers are also available in commercial fingerprint scanners sold by Seimens, Lucent, and Harris Semiconductor. Such silicon transducers measure capacitance. This requires the silicon transducers to be thin, reducing their durability. To detect a rolled fingerprint, the sensing array of the solid-state transducer needs to have an area of sufficient size, for example one-inch by one-inch with a thickness of about 50 microns. A silicon array with such a large size increases the base cost of a fingerprint scanner and leads to greater maintenance costs. Durability and structural integrity are also more likely to suffer in such a large silicon geometry.

What is needed is an inexpensive, durable fingerprint scanner with low maintenance costs.

SUMMARY OF THE INVENTION

The present invention provides a piezoelectric film biometric sensing device. A piezoelectric film sensor array is used to detect biometric data, for example, a fingerprint image. In one embodiment the piezo film sensor array is a multi-layer structure that includes a piezo layer sandwiched by two conductor grids. The conductor grids are oriented orthogonally to one another. A shield layer can be added to one side where a finger is placed to provide a protective coating. A foam substrate can be used as a support.

In one example, the piezo layer comprises a polarized fluoropolymer film, such as polyvinylidene flouride (PVDF) film or its copolymers. Conductor grids are silver ink electrodes printed on opposite sides of the PVDF film A shield layer is made of urethane or other plastic. A foam substrate is made of Teflon™. An adhesive holds the shield layer and foam substrate on opposite sides of the printed PVDF film.

In one feature, the PVDF film, including the printed electrodes, can be peeled off like a label for easy replacement.

According to one embodiment, a fingerprint scanner uses a piezo film sensor array to scan and capture an image of a fingerprint. The fingerprint scanner further includes an oscillator, gate counter, pulser, two multiplexers, controller, detector, filter and image memory. An input pulse of one cycle of the oscillator frequency (e.g., 30 MHZ) is applied by the pulser through a multiplexer to a single pixel or group of pixels in the piezo sensor array. A reflection from a ridge can be detected within a number of cycles after the input pulse is applied by the pulser. The presence of a fingerprint ridge is detected by virtue of a ring-down oscillation. The ring-down oscillation arises from reflections that occur when an electric field is applied to the piezoelectric thin film sensor array at a pixel in contact with the fingerprint ridge. A single pixel or a group of pixels is then detected and output to an image memory. The controller switches the multiplexers to scan the piezo film sensor array in coordination with the cycles of pulses output from the pulser and the detected pixel readings made by the detector.

Other reflections indicative of additional biometrics related to the finger (e.g. from tissue, blood, bone, fingernail, etc.) can also be detected. A Doppler effect due to reflections from circulating blood can also be detected. Such a Doppler effect can provide further information about direction and speed of blood circulation.

According to another embodiment, an instantaneous pyroelectric effect can also be detected by the piezoelectric film sensor array to indicate a live finger presence. A signal indicative of the live finger detection can then be used to automatically initiate or "awaken" the fingerprint scanner to scan and capture an image of the fingerprint using the same piezoelectric scanner array.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated herein and form part of the specification, illustrate the present invention and, together with the description, further serve to explain the principles of the invention and to enable a person skilled in the pertinent art to make and use the invention.

The present invention is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE EMBODIMENTS

1. Overview and Terminology

According to the present invention, a piezoelectric film biometric data sensing device is provided. The biometric sensing device can be, for example, a fingerprint scanner. A piezoelectric film sensor array is used to detect biometric data, for example, a fingerprint image.

The terms "piezoelectric" and "piezo" are used interchangeably herein to refer to the piezoelectric effect found in certain materials, including but not limited to piezoelectric polymer materials.

The term "conductor grid" as used herein is meant to refer to a pattern of conductors and includes, for example, a plurality of conductors arranged in parallel.

2. Piezoelectric Film Sensor Array

Figure 1A:
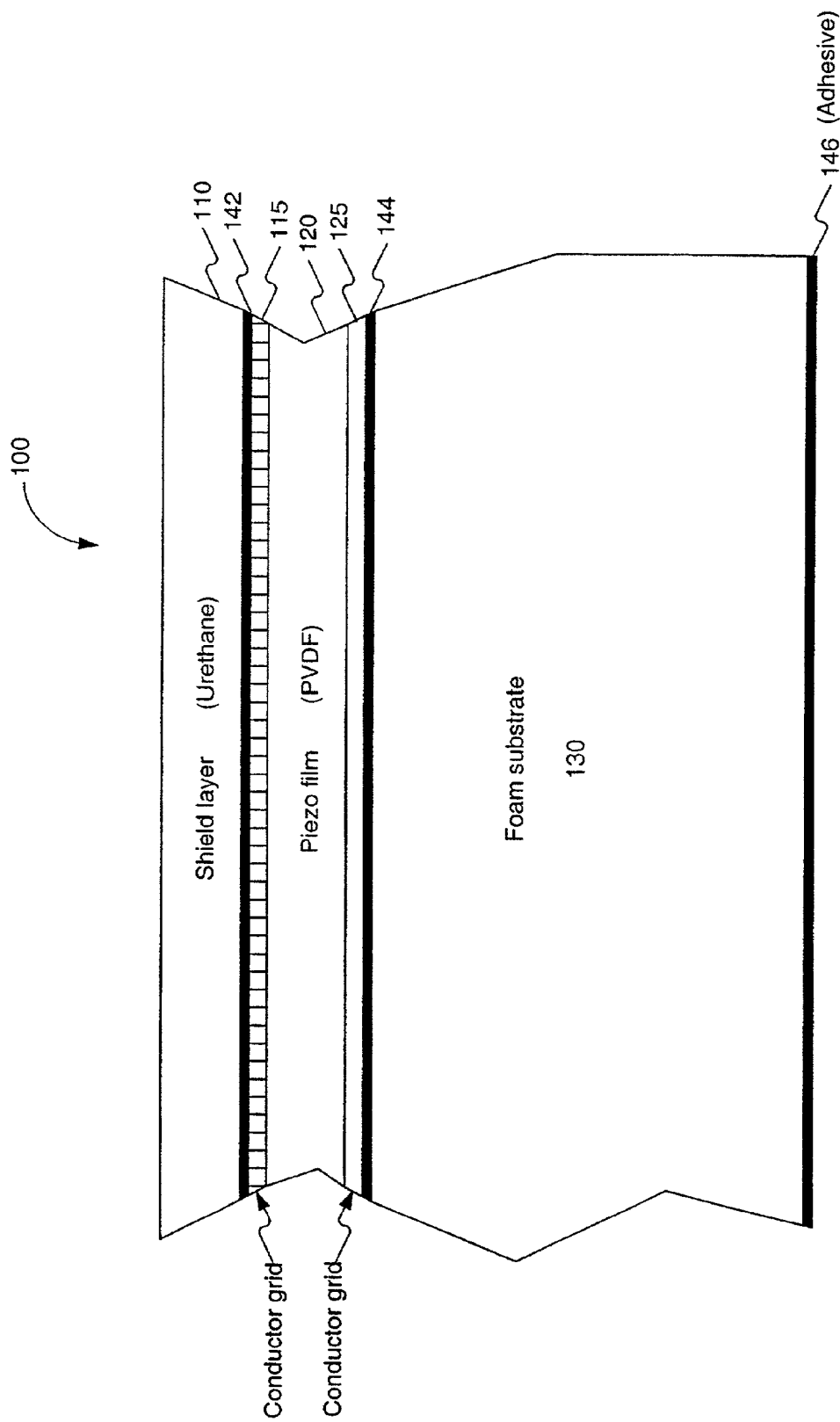
FIG. 1A is a cross-sectional view of a piezoelectric film sensor array according to one embodiment of the present invention.

FIG. 1A is a cross-sectional view of a piezoelectric film sensor array 100 according to one embodiment of the present invention. Piezoelectric film sensor array 100 is a multi-layer structure that includes a piezo film 120 sandwiched between two conductor grids 115, 125. Piezo film in one example of the instant invention is a polarized fluoropolymer film, such as polyvinylidene fluoride (PVDF) or its copolymers.

Figure 1B:
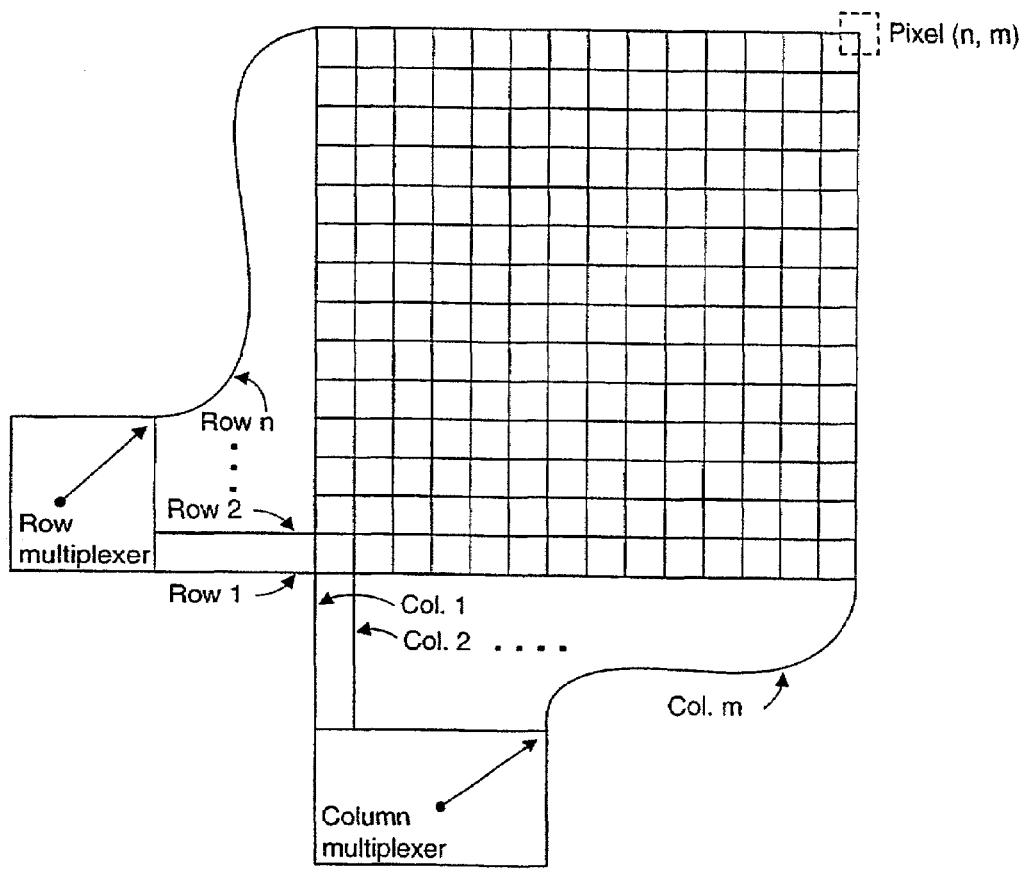
FIG. 1B is an overhead diagram illustrating the conductor grids of a piezoelectric film sensor array according to one embodiment of the present invention.

Conductor grids 115 and 125 each include parallel electrically conductive lines. Preferably, the lines of grid 115 are oriented orthogonally with respect to the lines of grid 125. This relationship is shown in FIG. 1B. FIG. 1B is an overhead diagram illustrating the conductor grids of a piezoelectric film sensor array according to one embodiment of the present invention. As seen in FIG. 1B, the two conductor grids are arranged orthogonally to one another such that a first of the two grids may be characterized as including conductive rows 1 to n, while a second of the two grids may be characterized as including conductive columns 1 to m. These conductive rows and columns are connected to respective associated row and column multiplexers, which will be discussed in greater detail below. Pixels within the array are the regions associated with points where ones of the rows cross ones of the columns. For example, the region where row n crosses column m corresponds to a pixel (n, m). In one example, conductor grids 115, 125 are silver ink electrodes printed on opposite sides of the PVDF film 120.

Returning to FIG. 1A, shield layer 110 can be added as a protective coating to a side where a finger is placed. Shield layer 110 can be made of urethane or another plastic capable of acting as a protective coating. Shield layer 110 can be affixed to conductor grid 115 and piezo film 120 with an adhesive 142. Materials suitable for use as such an adhesive are known to those skilled in the art and so the selection of an appropriate adhesive material is within the ordinary level of skill in the relevant art given this disclosure.

Foam substrate 130 can be used as a support within the piezo sensor array 100. Foam substrate 130 can be made of Teflon™. Other types of supportive material can be used in place of foam substrate 130, as would be apparent to a person skilled in the relevant art given this disclosure. Foam substrate 130 can be affixed to the conductor grid 125 and the piezo film 120 with an adhesive layer 144. Materials suitable for use as such an adhesive are known to those skilled in the art and so the selection of an appropriate adhesive material is within the level of skill in the art given this disclosure.

The above description is illustrative and not intended to limit the present invention. For example, piezo layer 120 can be any material exhibiting a piezoelectric effect including, but not limited to, piezoelectric polymers. Conductor grids 115, 125 can be any electrically conductive material including, but not limited to, metals. Likewise, other types of protective material can be used for shield layer 110 as would be apparent to a person skilled in the art given this description.

Piezoelectric polymer film sensors are further described in *Piezo Film Sensors: Technical Manual*, available from Measurement Specialities, Inc. Norristown, Pa., Apr. 2, 1999 REVB (incorporated by reference herein in its entirety).

3. Peel-Off Application

As an additional feature of the present invention, the PVDF film, including the printed electrodes, can be peeled off like a label for easy replacement. As shown in FIG. 1, piezo sensor array 100 can be mounted by adhesive 146 onto wax-paper or other material (not shown) for easy peel off. Materials suitable for use as such an adhesive are known to those skilled in the art and so the selection of an appropriate adhesive material is within the level of skill in the art given this disclosure. This allows the piezo sensor to be installed and/or replaced simply and easily at minimum cost. Indeed, compared to optical and silicon technologies maintenance of the piezo sensor array 100 is trivial.

4. Piezoelectric Film Fingerprint Scanner

The present invention further uses piezo film technology to detect and capture biometric data. For example, a fingerprint image can be detected.

Figure 2:
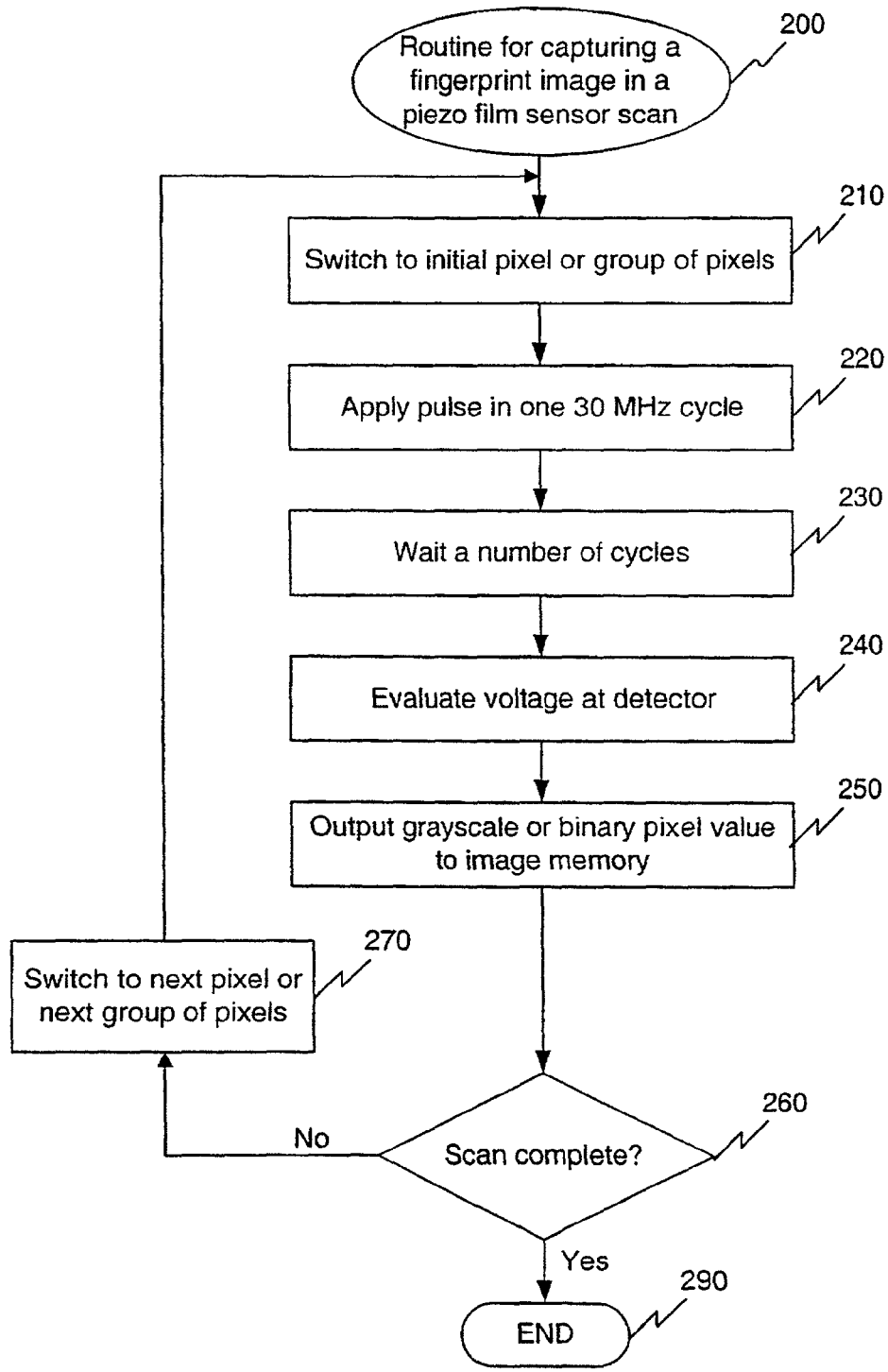
FIG. 2 is a flowchart showing a routine for capturing a fingerprint image in a piezoelectric film sensor array scan according to one embodiment of the present invention.
Figure 3:
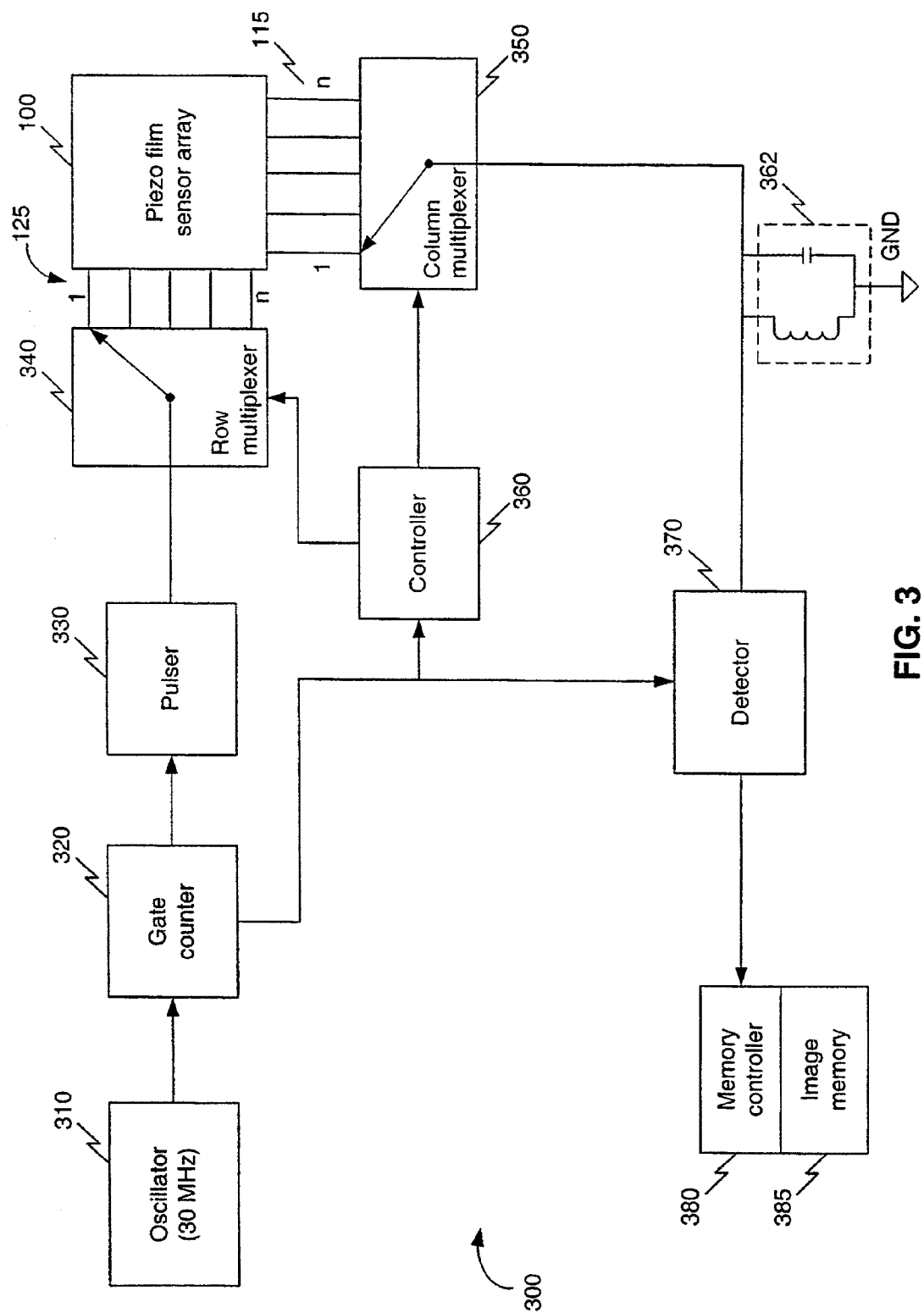
FIG. 3 is a block diagram of a piezoelectric film fingerprint scanner having a piezoelectric film sensor array according to one embodiment of the present invention.

The operation and structure of a piezoelectric film fingerprint scanner according to one embodiment of the present invention is described further with respect to FIGS. 2 and 3. FIG. 2 is a flowchart showing a routine 200 for capturing a fingerprint image in a piezoelectric film sensor-array scan according to one embodiment of the present invention (steps 210–290). FIG. 3 is a block diagram of a piezoelectric film fingerprint scanner 300 that includes piezo film sensor array 100 according to one embodiment of the present invention. Piezo film fingerprint scanner 300 includes oscillator 310, gate counter 320, pulser 330, row multiplexer 340, column multiplexer 350, controller 360, filter 362, detector 370, memory controller 380 and image memory 385. For clarity and in the interest of brevity, the steps of routine 200 are described in further detail with respect to the structure of FIG. 3. However, routine 200 is not so limited and other structure can be used as would be apparent to a person skilled in the art given the description herein.

In step 210, piezo film sensor array 100 is switched to detect an initial pixel or a group of pixels. In the example of FIG. 3, controller 360 switches row multiplexer 340 to a particular row or rows and column multiplexer 350 to a particular column or columns. In this manner, a particular associated pixel or group of pixels is designated as the initial pixel or group of pixels. For example, as shown in FIG. 1B, if the row multiplexer is switched to row n and the column multiplexer is switched to column m, pixel (n, m) is designated. In one example, piezo film sensor array is a 512×512 pixel array. Multiplexers 340 and 350 are each addressed by nine digit binary numbers to select a particular grid line at a designated address of the initial pixel or group of pixels being detected.

In step 220, a pulse is applied in one 30 MHz cycle. Oscillator 310 generates an oscillation signal at 30 MHz. This oscillation signal is applied to gate counter 320. Gate counter 320 then initiates purser 330 to send an input pulse to row multiplexer 340. Gate counter 320 also sends a signal to controller 360 and detector 370 indicating a count of the number of cycles. Controller 360 is coupled to row multiplexer 340 and a column multiplexer 350. Controller 360 sends signals to row multiplexer 340 and 350 that cause an initial particular pixel or group of pixels to be selected by the multiplexers 340, 350. Row multiplexer 340 forwards the input pulse to the initial pixel or group of pixels. Due to the piezoelectric characteristic of the piezo film, the pulse causes an oscillation at the pixel or pixels where the pulse is applied.

In step 230, piezo fingerprint scanner 300 waits a number of cycles before detecting a signal at the pixel. For example, in response to the signal sent from gate counter 320, detector 370 waits a number of cycles after the pulse is applied to the pixel (or group of pixels). Detector 370 is coupled to column multiplexer 350 and a filter circuit 362. In step 240, when the wait is complete the voltage at the initial pixel or group of pixels selected by column multiplexer 350 is evaluated at detector 370.

For example, one 30 MHz cycle corresponds to approximately 33 nanoseconds. The wait can be approximately 5 cycles or 150 nanoseconds. Other wait durations (e.g. a greater or smaller number of periods) can be used depending upon the oscillator frequency and/or other design considerations that would be apparent to a person skilled in the relevant art given this disclosure. This wait allows the ring down oscillation due to the presence of a fingerprint ridge to occur in response to the applied electrical pulse at the pixel.

In step 240, a filtered voltage is evaluated by detector 370 and a gray scale or a binary pixel value is output representative of the detected voltage (step 250). Filter circuit 362 is a band-pass filter that filters the output voltage to detect an output voltage signal in a passband centered about a frequency of approximately 30 MHz. The gray scale or binary pixel value is output to memory controller 380 for storage in an image memory 385. In one example, the output gray scale or binary pixel value is stored in an address in image memory 385 that corresponds to the detected pixel.

In step 260, a check is made to determine if the scan is complete. In other words, a check is made to determine whether each pixel in the 512×512 sensor array 100 has been scanned and a corresponding output value has been stored and accumulated in image memory 385. If the scan is complete, then the routine ends (step 290). A signal or other indication can then be generated and output from scanner 300 to indicate that a fingerprint image has been successfully captured. If the scan is not complete, then the piezo film sensor array 100 is switched to detect the next pixel or next group of pixels (step 270). Control then returns to perform steps 220 through 250 at the next pixel or next group of pixels.

Multiple Pixel Hits

As described above in steps 210 and 270, piezo film sensor array 100 can be switched by multiplexers 340 and 350 to detect voltage values at a single pixel or a group of pixels. In general, any pattern for scanning pixels can be used. For example, a raster scan of pixels can be performed. Pixels can be scanned row by row or column by column.

In one preferred example, when multiple groups of pixels are read out at a given instant, each pixel in a group of pixels are separated by a predetermined distance. In this way, interfering effects from the ring down oscillation in neighboring pixels are minimized or avoided. In one example, pixels detected in a given cycle are separated by a minimum distance of at least 8 pixels. In this way any ring down oscillations between neighboring pixels are attenuated significantly.

Other Implementations

Piezoelectric fingerprint scanner 300 as described above with respect to FIG. 3 is illustrative and not necessarily intended to limit the present invention. As it would be apparent to a person skilled in the art other implementations are possible given this description. For example, filter circuit 362 can be tuned as desired to remove noise and other oscillations. Filter circuit 362 can be a LC circuit or other type of filter circuit. Multiplexers 340 and 350 can be any type of multiplexer. For example, a single 1 to N multiplexer or multiple stages of multiplexers can be used. Oscillator 310 can be any type of oscillator, including but not limited to, a simple LC oscillator, variable-frequency oscillator, tunable oscillator, or crystal oscillator. In one preferred example, the oscillator is a radio-frequency 30 MHz oscillator. Other oscillation frequencies could be used as would be apparent to one skilled in the relevant art given this disclosure. Detector 370 can include an analog-to-digital converter (ADC) for output to a processor (e.g. a CPU) to support additional processing and control.

In general, control for carrying out routine 200 can be implemented in software, firmware, hardware, or any combination thereof. Such implementation would be apparent to a person skilled in the relevant art given this disclosure.

Fingerprint Ridge Detection

Figure 4A:
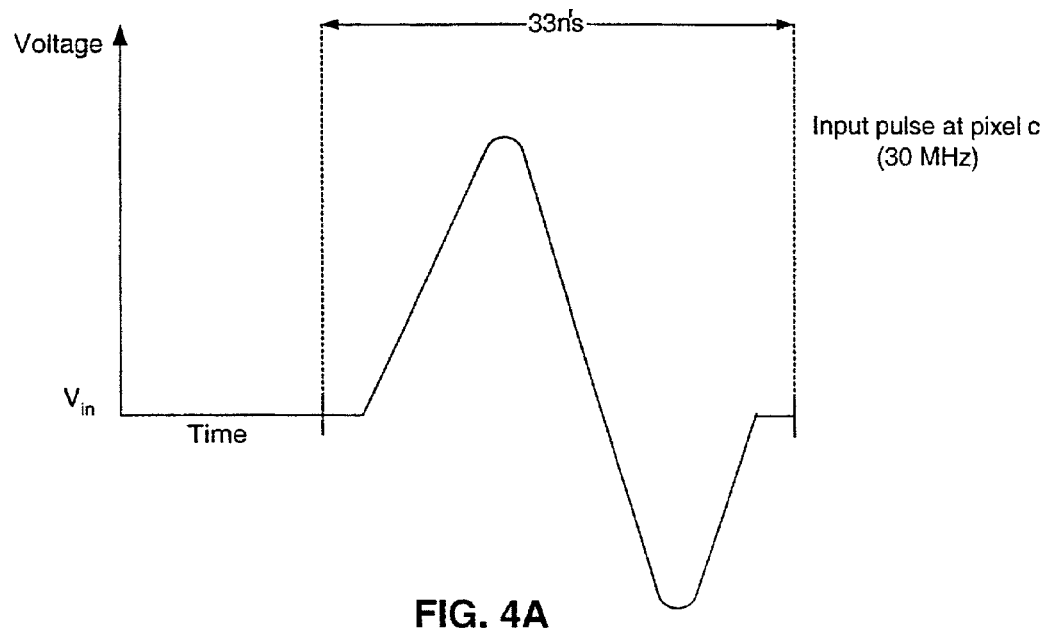
FIGS. 4A and 4B are plots of an example input pulse and detected output signal with ring-down oscillation according to the present invention.
Figure 4B:
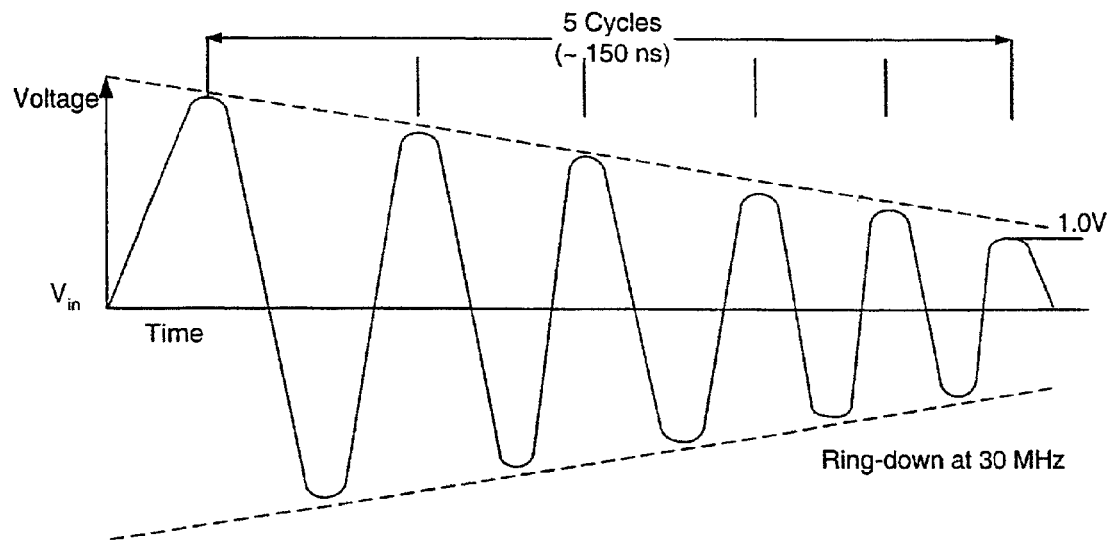
Figure 5:
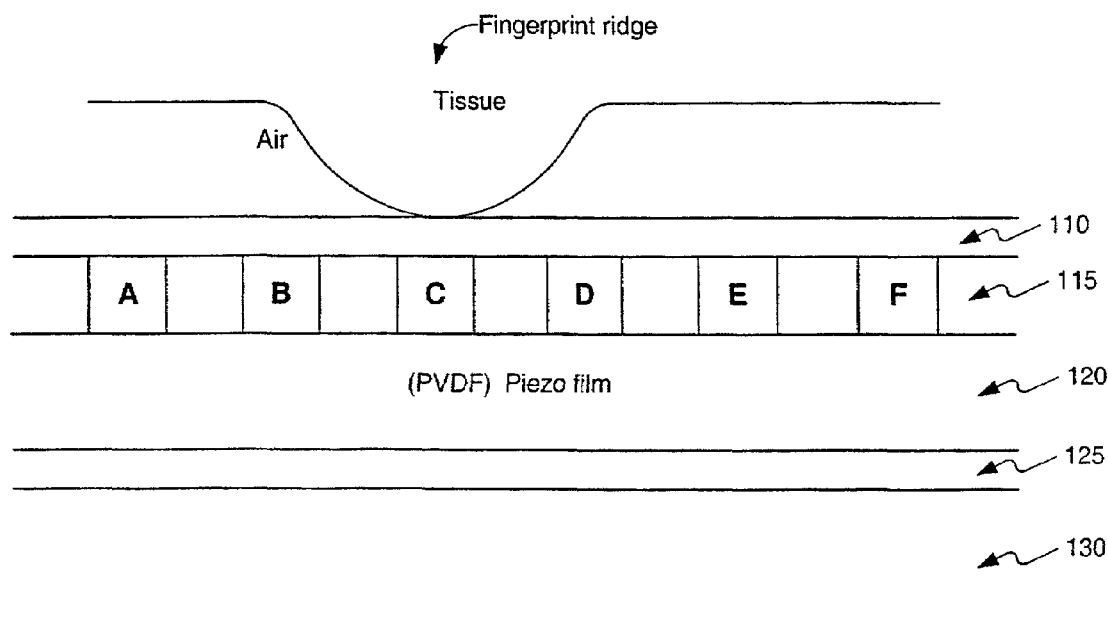
FIG. 5 is a cross-sectional view of a piezoelectric film sensor array having a fingerprint ridge (not to scale) in contact with the sensor array.

FIGS. 4A, 4B and 5 illustrate how fingerprint scanner 300 uses ring-down oscillation in piezo film sensor array 100 to detect a fingerprint ridge at a pixel C according to the present invention. Multiplexers 340 and 350 are switched to the address of pixel C (step 210 or 270). An input pulse in one 30 MHZ cycle is applied by pulser 330 (step 220). As shown in FIG. 4A, the voltage of the pulse (and consequently the electric field applied to pixel C) varies sinusoidally. The varying electric field causes the piezo layer 120 to likewise stress and unstress in an oscillating fashion. The stress on the piezo layer 120 creates wave energy. Such wave energy is reflected on the substrate side of piezo sensor array 100 at the interface with air. The wave energy is likewise reflected at the shield layer boundary when air is present. However, when a fingerprint ridge is present at pixel C, as shown in FIG. 5, creating a non-reflecting or transmissive boundary for the wave energy is created. This causes a ring-down oscillation to occur. This ring-down oscillation dampens over time due to inherent friction in the piezo film sensor array 100.

FIG. 4B shows a plot of an example detected output signal at pixel C with ring-down oscillation according to the present invention. The plots of FIGS. 4A and 4B are illustrative sketches and are not drawn to scale to represent actual signal outputs. As shown in FIG. 4B, after a wait of approximately five 30 MHZ cycles (or about 150 ns), a detector signal output can be filtered and detected to indicate the presence of a fingerprint ridge at pixel C. If the fingerprint ridge were not in contact at pixel C, ring-down oscillation would not occur. The filtered detector signal output would equal zero or at least be below a minimum voltage.

Extended Range and Other Biometric Information

Figure 6:
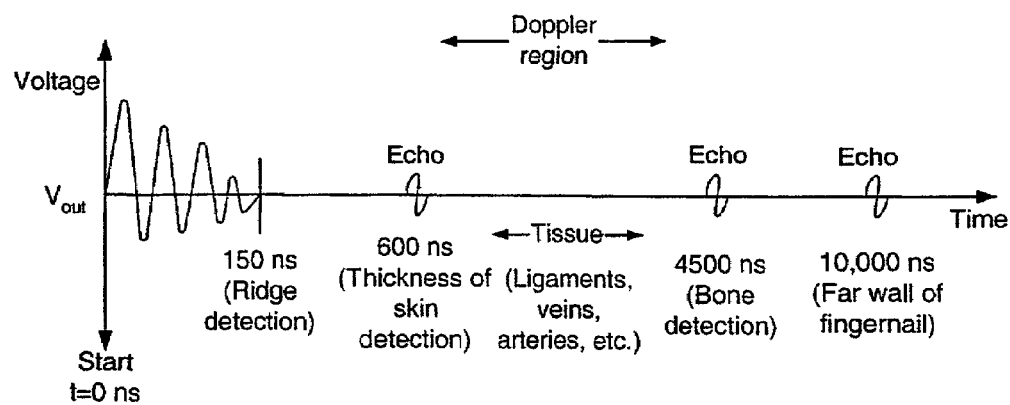
FIG. 6 is a plot of an example output signal with an extended range that shows other reflections indicative of further biometric information according to another embodiment of the present invention.

Other reflections indicative of additional biometrics related to the finger (e.g. from tissue, blood, bone, fingernail, etc.) can also be detected. A Doppler effect due to reflections from circulating blood can also be detected. Such a Doppler effect can provide further information about direction and speed of blood circulation. FIG. 6 is a plot of an example output signal with an extended range that shows other reflections indicative of further biometric information according to another embodiment of the present invention.

Live Finger Presence Detection Based on Pyroelectric Effect

According to another embodiment, an instantaneous pyroelectric effect can also be detected by the piezoelectric film sensor array to indicate a live finger presence. A signal indicative of the live finger detection can then be used to automatically initiate or "awaken" the fingerprint scanner to scan and capture an image of the fingerprint using the same piezoelectric scanner array.

CONCLUSION

While various embodiments of the present invention have been described above, it should be understood that they have been presented by way of example only, and not limitation. It will be understood by those skilled in the art that various changes in form and details may be made therein without departing from the spirit and scope of the invention as defined in the appended claims. Thus, the breadth and scope of the present invention should not be limited by any of the above-described exemplary embodiments, but should be defined only in accordance with the following claims and their equivalents.

What is claimed is:

1. A piezoelectric film fingerprint scanner comprising:
   an oscillator that generates an oscillation signal;
   a gate counter coupled to said oscillator that counts cycles of said oscillation signal generated by said oscillator;
   a controller coupled to said gate counter and each of a row multiplexer and a column multiplexer, said controller controls said row and column multiplexers responsive to said gate counter;
   a pulser coupled between said gate counter and said row multiplexer, said pulser sends an input pulse of one cycle of said oscillation signal to said row multiplexer;
   a piezo film sensor array including a first conductor grid coupled to said row multiplexer and a second conductor grid coupled to said column multiplexer, said first and second conductor grids disposed on first and second respective sides of said piezo film; and
   a voltage detector coupled to said gate counter and to said column multiplexer, said detector detecting a voltage corresponding to a pixel or group of pixels of said piezo film sensor array selected by said row and column multiplexers;
   wherein the voltage detector is configured to detect the voltage a predetermined number of cycles after the pulser sends the input pulse.

2. The piezoelectric film fingerprint scanner of claim 1, further comprising image memory that stores at least one of a gray scale and a binary detected pixel value from a memory controller unit, said memory controller unit coupled between said image memory and said detector.

3. The piezoelectric film fingerprint scanner of claim 1, wherein said oscillator unit generates a 30 MHz oscillation signal.

4. The piezoelectric film fingerprint scanner of claim 1, wherein said gate counter initiates said pulser to send an input pulse to said row multiplexer.

5. The piezoelectric film fingerprint scanner of claim 1, wherein detection of a reflection from a fingertip ridge is representative of a ring-down oscillation over a number of cycles of said oscillation signal.

6. A method for producing biometric data in a piezoelectric film sensor comprising the steps of:
   (1) applying a generated oscillation signal to a gate counter;
   (2) switching a piezo film sensor array to detect at least one of an initial pixel and a group of pixels;
   (3) initiating a pulser to send an input pulse to one of a plurality of multiplexers in response to said gate counter;
   (4) waiting a number of cycles after the input pulse is applied to the one of a pixel and a group of pixels to detect a signal at the pixel;
   (5) measuring an output filtered voltage at a voltage detector as one of a gray scale and a binary pixel; and
   (6) storing said one of a gray scale and a binary pixel values in an image memory.

7. The device of claim 6, wherein the biometric data represents a portion of a fingerprint pattern.

8. The device of claim 6, wherein the biometric data represents a portion of a fingerprint ridge.

9. The device of claim 6, wherein the biometric data represents a portion of an arteriole-veinal map.

10. The device of claim 6, wherein the biometric data represents a portion of a bone map.

11. The device of claim 6, wherein the biometric data represents blood flow.

12. The device of claim 6, wherein the biometric data represents arteriole blood flow.

13. The device of claim 6, wherein the biometric data represents capillary blood flow.

14. The device of claim 6, wherein the biometric data represents a ratio of arteriole and capillary blood flow.

* * * * *